United States Patent [19]

Morton, Jr.

[11] 4,108,878
[45] Aug. 22, 1978

[54] PGD$_2$ ANALOGS

[75] Inventor: Douglas Ross Morton, Jr., Portage, Mich.

[73] Assignee: The Upjohn Company, Kalamazoo, Mich.

[21] Appl. No.: 756,096

[22] Filed: Jan. 3, 1977

Related U.S. Application Data

[62] Division of Ser. No. 614,242, Sep. 17, 1975, Pat. No. 4,016,184.

[51] Int. Cl.$^2$ .......................................... C07C 177/00
[52] U.S. Cl. .................................... 260/408; 260/410; 260/410.5; 260/410.9 R; 260/413; 260/514 D; 560/121
[58] Field of Search ............. 260/468 D, 514 D, 408, 260/410, 410.5, 410.9 R, 413; 560/121

[56] References Cited

U.S. PATENT DOCUMENTS

| | | | |
|---|---|---|---|
| 3,878,239 | 4/1975 | Hayashi et al. | 260/514 |
| 3,914,282 | 10/1975 | Pike | 260/468 |
| 3,932,463 | 1/1976 | Schaub et al. | 260/340.7 |
| 3,933,889 | 1/1976 | Magerlin | 260/468 |
| 3,933,899 | 1/1976 | Nelson | 260/473 |
| 3,959,346 | 5/1976 | Schneider | 260/468 |
| 3,962,293 | 6/1976 | Magerlin | 260/408 |
| 4,026,909 | 5/1977 | Yankel | 260/408 |

OTHER PUBLICATIONS

Burger, Medicinal Chemistry, pp. 81, 82 (1960).

Primary Examiner—Robert Gerstl
Attorney, Agent, or Firm—Robert A. Armitage

[57] ABSTRACT

Prostaglandin analogs with the following cyclopentane ring structure:

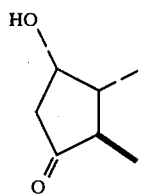

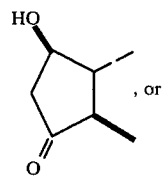

, or

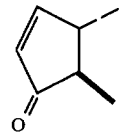

are disclosed along with intermediates useful in their preparation and processes for their preparation. These analogs are useful for the same pharmacological purposes as the prostaglandins, particularly and especially as blood platelet aggregation inhibitors.

16 Claims, No Drawings

PGD₂ ANALOGS

The present application is a divisional application of Ser. No. 614,242, filed Sept. 17, 1975, now issued as U.S. Pat. No. 4,016,184, on Apr. 5, 1977.

The present invention relates to prostaglandin analogs for which the essential material constituting a disclosure therefor is incorporated by reference here from U.S. Pat. No. 4,016,184, issued Apr. 5, 1977.

I claim:

1. A prostaglandin analog of the formula

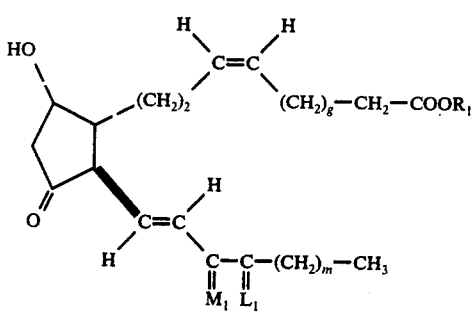

wherein $g$ is one, 2, or 3;

wherein $m$ is one to 5, inclusive;

wherein $M_1$ is

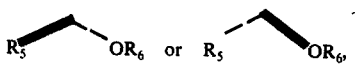

wherein $R_5$ and $R_6$ are hydrogen or methyl, with the proviso that one of $R_5$ and $R_6$ is methyl only when the other is hydrogen;

wherein $L_1$ is

or a mixture of

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein $M_1$ is

3. A compound according to claim 1, wherein $M_1$ is

4. A compound according to claim 3, wherein $m$ is 3.
5. A compound according to claim 4, wherein $g$ is 3.
6. A compound according to claim 5, wherein $R_5$ and $R_6$ are both hydrogen.
7. A compound according to claim 6, wherein $R_3$ and $R_4$ are both hydrogen.
8. 2a,2b-Dihomo-cis-4,5-didehydro-PGD₁, a compound according to claim 7.
9. A compound according to claim 6, wherein $R_3$ and $R_4$ are both fluoro.
10. 2a,2b-Dihomo-16,16-difluoro-cis-4,5-didehydro-PGD₁, a compound according to claim 9.
11. A compound according to claim 4, wherein $g$ is one.
12. A compound according to claim 11, wherein $R_5$ and $R_6$ are both hydrogen.
13. A compound according to claim 12, wherein $R_3$ and $R_4$ are both hydrogen.
14. cis-4,5-Didehydro-PGD₁, a compound according to claim 13.
15. A compound according to claim 12, wherein $R_3$ and $R_4$ are both fluoro.
16. 16,16-Difluoro-cis-4,5-didehydro-PGD₁, a compound according to claim 15.

* * * * *